United States Patent [19]

Ball

[11] Patent Number: 4,909,879
[45] Date of Patent: Mar. 20, 1990

[54] METHOD FOR THE CODING OF ABSORBENT MATERIAL

[75] Inventor: Jeffrey M. Ball, Manchester, England

[73] Assignee: Willett International Limited, High Wycombe, England

[21] Appl. No.: 291,332

[22] Filed: Dec. 23, 1988

Related U.S. Application Data

[63] Continuation of Ser. No. 883,813, Jul. 9, 1986, abandoned.

[30] Foreign Application Priority Data

Jul. 9, 1985 [GB] United Kingdom ............. 8517318

[51] Int. Cl.$^4$ .............................................. B32B 31/08
[52] U.S. Cl. ................................... 156/164; 156/277; 604/361
[58] Field of Search .............. 156/384, 277, 160, 163, 156/164, 176, 229; 604/361, 358; 106/20, 21, 22, 23

[56] References Cited

U.S. PATENT DOCUMENTS

| | | | |
|---|---|---|---|
| 3,666,611 | 5/1972 | Joa | 604/358 |
| 3,759,261 | 9/1973 | Wang | 604/361 |
| 3,868,287 | 2/1975 | Lewyckyj | 604/358 |
| 4,022,211 | 5/1977 | Timmons et al. | 604/361 |
| 4,081,301 | 3/1978 | Buell | 156/164 |
| 4,186,020 | 1/1980 | Wachtel | 106/21 |
| 4,303,924 | 12/1981 | Young | 106/22 |
| 4,365,998 | 12/1982 | Sugiyama et al. | 106/22 |
| 4,389,503 | 6/1983 | Maxwell et al. | 106/22 |
| 4,512,807 | 4/1985 | Ogawa et al. | 106/22 |

FOREIGN PATENT DOCUMENTS 0011274 7/1985 European Pat. Off. .
1486414 9/1977 United Kingdom .

Primary Examiner—Merrell C. Cashion, Jr.
Attorney, Agent, or Firm—Charles D. Gunter, Jr.

[57] ABSTRACT

The present invention provides a process for marking a diaper fabric which comprises applying to the fabric one or more images by means of an ink jet printing technique during the fabrication of the diaper from its component materials. Preferably, the invention is used to apply a fluid indicator fluid to that face of the impervious layer to be in contact with the absorbent layer during the manufacture of the composite diaper fabric, the other face of the absorbent layer being that which is to be directly or indirectly in contact with a wearer of the diaper. It is also preferred that the indicator fluid comprise a water-soluble dyestuff whereby the indicator is rendered mobile upon contact with a fluid.

The invention further provides a diaper having an image formed thereon, preferably on that face of the impervious layer in contact with the absorbent layer, which image comprises a series of dots configured to form the desired image, preferably the image is formed from a water-soluble dyestuff.

8 Claims, 1 Drawing Sheet

U.S. Patent  Mar. 20, 1990  4,909,879
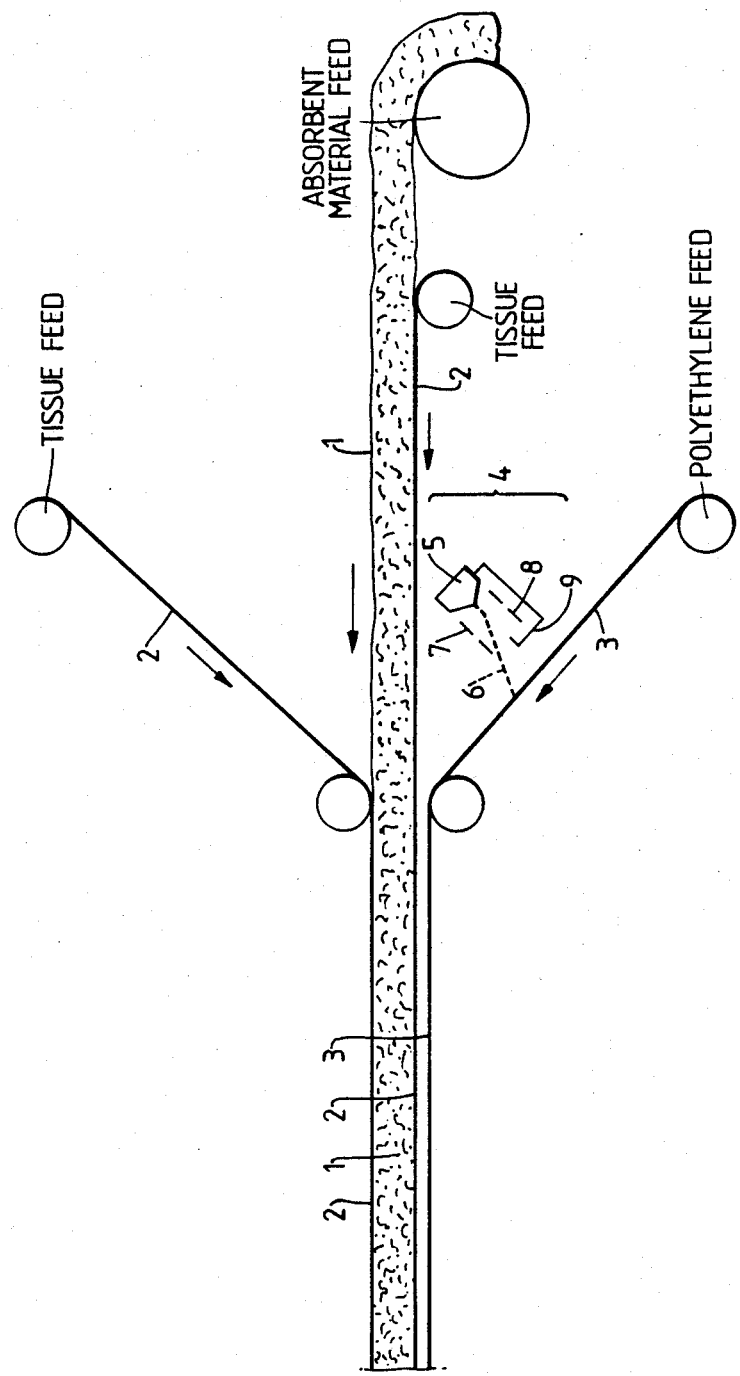

METHOD FOR THE CODING OF ABSORBENT MATERIAL

This application is a continuation, of application Ser. No. 883,813, filed 07/09/86, now abandoned.

The present invention relates to the coding of absorbent materials, notably to the marking of manufacturing and other codes on a diaper, particularly to provide a fluid mobile marking to indicate when the diaper has been wetted.

In the production of diapers, a layer of an absorbent material such as a flocked, felted or needled fabric, tissue or reticulated material or cotton wool-like material is combined with an impervious material, the absorbent layer being designed to absorb urine and other body fluids from the person wearing the diaper and the outer layer being designed to prevent escape of these from the absorbent layer into the environment. Whilst the final form of the finished diaper may differ from manufacturer to manufacturer, the above construction of the diaper fabric is common to substantially all designs of diaper and is produced by similar techniques.

It would be desirable to be able to print date, quality control and other manufacturing codes on each batch of diaper fabric and to give each individual diaper the manufacturer's brand name or other indicia to aid marketing of the diapers. However, the lengths of material which are to be combined to form the composite diaper fabric travel at high speeds and it would be necessary to ensure accurate registration of the printing with the fast moving material so that the printed images occur at the desired location on each diaper. This is difficult and any relative movement between the printing head and the material being printed would cause blurring of the image. Furthermore, the fluffy nature of the absorbent layer would cause major problems due to fluff contamination of the printing head. It has been therefore been proposed to use pre-printed material carrying random images on the material so as to avoid the need for accurate registration between the various components used to make up the diaper fabric. However, this requires that a production line be designated to a given product or that the operation of that line must be interrupted to change from one feed of pre-printed material to another where it is desired to change the image in the diaper fabric being produced.

We have found that ink jet printing tehniques provide an advantageous method for marking quality control codes and the like onto a diaper during its manufacture, notably onto the inner face of the impervious layer of the diaper fabric. An ink jet printer is a non-contact type of printer and reduces problems due to fluff contamination and snagging of the material being printed with the print head which occur with contact type printers as used hitherto. Furthermore, an ink jet printer produces an image which can be readily altered without the need to close down a printing line to change printing plates and the like, thus enabling a manufacturer to vary the image produced to suit a purchaser's individual requirements and to switch between one image and another at will without having to stop the diaper fabric production line. The print head for an ink jet printer is compact and therefore can readily be incorporated into a diaper fabric production line without disruption of the layout of the line or interference with other operations in the production line. Furthermore, an ink jet printer can operate at high speeds to secure accurate positioning of the image on a fast moving component of the diaper fabric immediately prior to that component being incorporated into the diaper fabric, thus reducing the problems of registration of the image with the diaper fabric.

Accordingly, the present invention provides a process for marking a diaper which comprises applying one or more images to one or more components of the diaper by means of an ink jet printing technique. The Figure illustrates the method steps of the claimed invention. Preferably, the invention is used to apply an indicator fluid to that face of the impervious layer of a composite diaper fabric to be in contact with the absorbent layer, the other face of the absorbent layer being that which is to be directly or indirectly in contact with a wearer of the diaper. Preferably, such application takes place during the process of manufacture of the composite diaper fabric rather than during the fabrication of the individual components for subsequent use in the manufacture of the composite fabric. It is also preferred that the indicator fluid contain a water-soluble dyestuff and that the indicator fluid be rendered mobile upon contact with a bodily fluid.

The invention further provides a diaper fabricated from a composite fabric having an image formed thereon, preferably on that face of the impervious layer in contact with the absorbent layer, which image comprises a series of dots configured to form the desired image. Preferably the image is formed from a water-soluble dyestuff.

The invention can be applied to all types of diaper and to form any desired image on the diaper. Thus, the invention can be applied in the manufacture of incontinence pads, as well as to diapers for infants. The term diaper is therefore used herein to denote in general a composite construction comprising a liquid impervious layer having in association therewith a fluid absorbent layer adapted to be in contact directly or indirectly with a wearer of the diaper, the construction being in sheet, strip or pad form and intended for use upon the person. The term diaper fabric is used herein to denote this construction prior to cutting or otherwise forming the individual diapers therefrom.

The fluid applied to the diaper fabric can be one which is visible under UV light or one which carries magnetic particles to provide an image which can be scanned by a magnetic sensor for use in quality control or other manufacturing control operations. However, the invention is of special use in the application of a dyestuff to the diaper fabric to provide an image which can be used for marketing purposes and/or to provide an indicator which disperses or intensifies and/or changes in colour to indicate when the diaper has been wetted by the wearer. For convenience, the invention will be described hereinafter in terms of this preferred use and in terms of a diaper which comprises an absorbent layer comprising a cotton-wool-like cellulosic material as the absorbent material encased in a water permeable casing such as non-woven, felted, needled or similar tissue-like material, and a sheet plastic material mounted on one side of the absorbent layer to provide an outer impervious layer.

The diaper fabric can be manufactured by any suitable method. This will usually comprise bringing together lengths of the absorbent material, the casing for that material and the impervious layer on a continuous basis to form the basic diaper fabric. This is then subjected to such other treatments, eg. folding the fabric to adopt the desired configuration, applying side fastenings and so on, as may be required to form the individual diapers. The present invention is not restricted to any specific method by which the diaper fabric is formed nor its subsequent treatment and these can be of conventional nature. As indicated above, the invention is preferably applied to the material of the impervious layer as this is or is about to be incorporated with the other components into the composite diaper fabric.

The present invention therefore further provides in a diaper fabrication process a printer station located in association with the feed of one or more of the component materials for the diaper fabric and adapted to apply a fluid to the material by means of an ink jet printer. In the preferred embodiment of the invention, the printing station is located on the feed path of the impervious material so that it forms an image on that face of the material which is to be in contact with the absorbent layer in the composite diaper fabric. Thus, when the impervious material is combined with the absorbent layer or with the components used to form that layer to give the diaper fabric, the image is located between the impervious and absorbent layers and is protected from smearing or abrasion during subsequent handling or use by the impervious layer, but is visible through that layer.

The image can be formed by any suitable ink jet printing technique. Thus, the image can be formed using an on-demand printer in which droplets of ink are dispensed from an array of nozzles located across the line of travel of the fabric. Each nozzle is fed with ink, usually under pressure, through a valving means, eg. a solenoid valve. The sequence of operation of the valves is controlled by a micro-processor or the like so that they are actuated in the desired order to emit droplets to form the desired image. Typical of suitable ink jet printers of this type for present use are those sold by Willett Printos Limited as LCP printers.

Alternatively, the ink is dispensed continuously through a nozzle as a discrete single jet which passes through a charge electrode. The stream of ink is excited by applying a vibration thereto to break the stream up into substantially uniform droplets, eg. by exciting a piezo-electric crystal in contact with the ink. The charged droplets are passed through an electric field which causes the droplets to be deflected away from their natural flight path. The extent of deflection is controlled by the charge applied to the droplet and/or the strength of the deflecting field. Thus, the flight path of each droplet can be controlled so that it falls upon the desired location on the impervious material or into a catcher mechanism or gutter where it is desired that no image be printed with that droplet. Droplets falling into the gutter are re-cycled for re-use. Typical of such printers are those available as Willett Printos 1600 printers.

Other suitable ink jet printers include those in which the ink composition is drawn from the nozzle by electrostatic forces to give charged droplets which can be guided as described above; those where the droplets are drawn through the nozzles by capillary action; and those where the ink composition is heated within the printing head immediately adjacent the nozzle so as to form a vapour bubble which expels the ink through the nozzle.

The above forms of printer are characterised in that they are non-contact printers and hence do not crush or otherwise affect the structure of the diaper fabric nor do they present an obstruction to the free passage of material past the printing station. The operation of the printer can be closely synchronised with the movement of the substrate upon which printing is to take place. Hence, accurate registration of the printed images with the impervious material or the diaper fabric can be achieved, even where the speed of travel of the material being printed varies.

The image which is formed can be selected at will by the operator so as to identify a batch of diaper fabric for manufacture or quality control purposes. However, it is preferred that images be formed at appropriate intervals on the impervious material so that each individual diaper carries an image printed thereon which will vary when the diaper is wetted by a body fluid. The images formed by an ink jet printer are characterised by being composed of a number of dots, whereas conventional contact printing techniques, such as are proposed in for example U.S. Pat. No. 4,022,211, give continuous images which readily smudge if there is not complete co-ordination between the fabric being printed and the printing plattern.

The indicator fluid used to form the image can be of any suitable composition, for example it can be a solvent or water based ink. Preferably, the ink composition is one which is rendered mobile upon subsequent contact with body fluids so that the image forms a smudge visible through the outer impervious plastics layer when the wearer wets the diaper. This smudge provides a simple and effective indicator that the diaper has been wetted by the wearer. Alternatively, the ink composition can be one which develops a colour or intensifies and/or changes colour when contacted with a body fluid. It is therefore preferred that the indicator composition contain a physiologically acceptable water-soluble dyestuff, notably one which is a food grade material. The optimum composition for application to the diaper fabric will depend upon the intensity of colouration required both when dry and when wetted, and can be readily determined in each case. It is a further advantage of the use of an ink jet printer that the ink composition can be readily changed merely by using a secondary printing head without the need to halt the diaper fabrication process.

As indicated above, the composite diaper fabric can be subjected to further treatment to form the individual diaper units. It is also within the scope of the present invention to give the printed component one or more subsequent treatments before it is incorporated into the diaper fabric. Thus, the printed image can be dried to avoid the risk of smudging as the overall diaper fabric is built up or it can be printed with other images.

The invention will now be illustrated by the following Examples in which all parts and percentages are given by weight:

Example 1

A diaper fabric comprising an absorbent layer 1 of cotton wool-like material encased in a needled tissue like cellulosic material 2 and having an outer sheet polyethylene plastics impervious layer 3 was formed by feeding webs of the individual components through a conventional high speed diaper manufacturing line shown diagrammatically in the accompanying drawing. A Willett Printos 1600 continuous ink jet printer head 4 was located over the sheet feed of the polyethylene sheet so as to print dot matrix images thereon 16 dots high.

The printer head comprised a nozzle 5 fed with an ink composition to form a jet of fluid issuing from the nozzle. This jet was broken up into a series of discrete mono-sized and substantially uniformly spaced apart droplets 6 by excitement with a piezoelectric crystal acting on the ink.

At or above the point at which the jet broke up into droplets, was mounted a charge electrode 7 which applied a varying charge to the droplets. The charged droplets passed between a pair of charged deflection plates 8 which generated an electric field which caused the droplets to deflect from their free flight path by an amount which depended upon the charge carried by the droplet. The extent of deflection determined the position at which the droplet was deposited on the polyethylene web 3 and hence the image formed. Where it was desired not to deposit a droplet on the polyethylene sheet the droplet was not given a charge and followed its free flight path into a gutter or other catching means 9 which intercepted the path of the droplet. The droplets caught in the gutter were recycled for re-use.

The printer 4 used an ethanol based ink composition containing a food grade water-soluble blue dyestuff. The resultant diapers each possessed a clearly visible blue image formed from a series of dots on the inner surface of the polyethylene layer 3.

When worn by a small child, the image could be seen without removing the diaper. When the child wetted the diaper, the image became smudged and provided a clearly visible indication of when the diaper needed changing.

Example 2

The process of Example 1 was repeated except that the ink composition was a water/ethanol based composition containing a polymeric binder to provide a composition which rapidly dried upon application to the polyethylene sheet. When the printed image from such a composition was wetted, the dyestuff dispersed and the image faded in the wetted area.

Example 3

The process of Example 1 was repeated except that the coloured dyestuff was replaced with a colourless but UV fluorescent agent. The resultant image on the diaper fabric could be read under UV illumination for quality control purposes but did not give an image which could be detected by a user under normal conditions.

What we claim is:

1. A method for marking a diaper which is fabricated from component materials as a composite construction comprising a substantially fluid impervious layer having in association therewith a fluid absorbent layer adapted to be in operative contact with a wearer of the diaper, which method comprises applying droplets of fluid during the fabrication of the composite construction from its component materials to a selected one of the component materials thereof, the fluid being applied by means of a non-contact ink jet printing technique which applies discreet droplets of the fluid through at least one nozzle orifice to individually selected positions on the selected component material so as to form a desired image on the selected component of the diaper.

2. A method as claimed in claim 1, wherein the fluid is a fluid indicator, the fluid indicator being applied to the fluid impervious layer of the composite construction.

3. A method as claimed in claim 1, wherein the non-contact ink jet printing technique utilizes a non-contact ink jet printer which is located on a feed path of the substantially fluid impervious material to a point at which the component materials are unified to form the composite diaper construction so that the non-contact ink jet printer forms an image on a selected face of the substantially fluid impervious material.

4. In a process for making a diaper fabric having a composite construction comprising a substantially fluid impervious layer formed from a polyethylene material and having in association therewith a fluid absorbent layer formed from a cellulosic fibrous material which fabric is subsequently to be formed into a diaper adapted to be worn upon the person with said absorbent layer being in operative contact with the person so as to absorb body fluids therefrom, which process comprises continuously feeding the elements of the composite fabric to a process in which they are unified into the said composite fabric, the improvement which comprises forming an image from a series of dots on that face of the said polyethylene sheet material to be in operative contact with said absorbent layer by applying thereto a fluid indicator composition by means of a non-contact ink jet printer located intermediate the feed of said material and its incorporation into the composite fabric, and further comprising the step of varying the image formed on the face of the polyethylene sheet material by varying the arrangement of the series of dots being applied by the non-contact ink jet printer while continuing to continuously feed the elements of composite fabric to the process.

5. A process as claimed in claim 4 in which said indicator composition comprises a water-soluble dyestuff whereby the image formed is caused to disperse when a diaper formed from the composite fabric is wetted by a wearer.

6. A method for making a diaper fabric having a composite construction which includes a substantially fluid impervious layer formed from a synthetic resilient sheet material having opposed faces and having in association therewith a fluid absorbent layer formed from a cellulosic fibrous material, which fabric is subsequently to be formed into a diaper adapted to be worn upon the person with said absorbent layer being contactable with the person so as to absorb body fluids therfrom, which method comprises feeding the components of the composite fabric to a process in which they are unified into the said composite fabric, and forming an image on a selected one of said components by applying droplets of a fluid to selected positions on said selected component by means of a non-contact ink jet printer apparatus which applies discreet droplets of the fluid through at least one nozzle orifice to an individually selected position on said component so as to form a desired image on the said component as said component is fed to the unification process.

7. The method of claim 6, wherein the image so formed is applied to that opposed face of said resilient synthetic sheet material which is to be in operative contact with said absorbent layer.

8. The method of claim 7, wherein the fluid is an indicator fluid which comprises a water-soluble dyestuff so that the image formed is capable of dispersing when a diaper formed from the composite fabric is wetted by a wearer.

* * * * *